US009211086B2

(12) United States Patent
Otsamo et al.

(10) Patent No.: US 9,211,086 B2
(45) Date of Patent: Dec. 15, 2015

(54) METHOD FOR INDICATING PHYSIOLOGICAL STRESS LEVEL AND RECOVERY FROM STRESS AND DEVICE TO BE UTILIZED IN METHOD

(75) Inventors: Katriina Otsamo, Oulu (FI); Minna Saloranta, Oulu (FI); Junnu Lukkari, Oulu (FI)

(73) Assignee: Juno Medical LLC, Oulu (FI)

( * ) Notice: Subject to any disclaimer, the term of this patent is extended or adjusted under 35 U.S.C. 154(b) by 310 days.

(21) Appl. No.: 13/878,812

(22) PCT Filed: Oct. 5, 2011

(86) PCT No.: PCT/FI2011/050858
§ 371 (c)(1),
(2), (4) Date: Jun. 13, 2013

(87) PCT Pub. No.: WO2012/049360
PCT Pub. Date: Apr. 19, 2012

(65) Prior Publication Data
US 2013/0289435 A1    Oct. 31, 2013

(30) Foreign Application Priority Data

Oct. 11, 2010    (FI) ..................................... 20106045

(51) Int. Cl.
*A61B 5/00*    (2006.01)
*A61B 5/11*    (2006.01)
(Continued)

(52) U.S. Cl.
CPC ................ *A61B 5/11* (2013.01); *A61B 5/4519* (2013.01); *A61B 5/4824* (2013.01);
(Continued)

(58) Field of Classification Search
CPC .... A61B 5/04; A61B 5/0488; A61B 5/04001; A61B 5/053; A61N 1/18
See application file for complete search history.

(56) References Cited

U.S. PATENT DOCUMENTS 7,254,444 B2    8/2007    Moore et al.
7,499,746 B2    3/2009    Buhlmann et al.
(Continued)

FOREIGN PATENT DOCUMENTS

CA    2159564 A1    3/1997
CN    1029505 C    8/1995
(Continued)

OTHER PUBLICATIONS

International Search Report for parent application PCT/FI2011/050858, having a mailing date of Feb. 16, 2012.
(Continued)

*Primary Examiner* — Max Hindenburg
(74) *Attorney, Agent, or Firm* — Andrus Intellectual Property Law, LLP

(57) ABSTRACT

A method and device arrangement are for indicating a state of overstress in a nervous muscular system. An interference current, the frequency and current strength of which can be adjusted, is fed into a part of the nervous muscular system. Those adjustment values of the interference current are stored, which cause one of a set of predetermined physical sensations in the examined part of the nervous muscular system. A measurement-specific average of the strength of the interference current is calculated for each predetermined physical response or sensation in the examined part of the examined nervous muscular system. The measurement-specific average of the interference current for each physical sensation is normalised and a state of overstress of the nervous muscular system is indicated, if the measurement-specific normalised average of the interference current of the physical sensation does not fulfil a set statistical criteria.

11 Claims, 4 Drawing Sheets

(51) Int. Cl.
*A61B 5/053* (2006.01)
*A61B 5/04* (2006.01)

(52) U.S. Cl.
CPC .......... *A61B 5/6824* (2013.01); *A61B 5/04001* (2013.01); *A61B 5/053* (2013.01); *A61B 5/6823* (2013.01); *A61B 5/6829* (2013.01)

(56) References Cited

U.S. PATENT DOCUMENTS

| | | | |
|---|---|---|---|
| 8,942,797 B2 * | 1/2015 | Bartol et al. ................. | 600/546 |
| 2005/0283204 A1 | 12/2005 | Buhlmann et al. | |
| 2010/0069796 A1 | 3/2010 | Duncan et al. | |

FOREIGN PATENT DOCUMENTS

| | | |
|---|---|---|
| CN | 101612450 A | 12/2009 |
| FI | 120575 B1 | 12/2009 |

OTHER PUBLICATIONS

Finnish Search Report for priority application FI 20106045, dated Jun. 13, 2011.

M. Yochum et al, "A Mixed FES/EMG System for Real Time Analysis of Muscular Fatigue", 32nd Annual International Conference of the IEEE EMBS, Buenos Aires, Argentina, Aug. 31-Sep. 4, 2010, pp. 4882-4885.

* cited by examiner

Fig. 3a

METHOD FOR INDICATING PHYSIOLOGICAL STRESS LEVEL AND RECOVERY FROM STRESS AND DEVICE TO BE UTILIZED IN METHOD

CROSS-REFERENCE TO RELATED APPLICATIONS

This application is the U.S. national stage application of International Application No. PCT/FI2011/050858, filed Oct. 5, 2011, which International application was published on Apr. 19, 2012 as International Publication No. WO 2012/049360 A1 in the English language and which application is incorporated herein by reference. The International application claims priority of Finnish Patent Application No. 20106045, filed Oct. 11, 2010, which application is incorporated herein by reference.

FILED

The invention relates to a method for indicating a state of overstress in a nervous muscular system, in which method an interference current, the frequency and current intensity of which can be adjusted, is fed into the nervous muscular system, those adjustment values of the interference current are stored, which cause one of a set of predetermined physical sensations in an examined part of the nervous muscular system, and whether the nervous muscular system has recovered from a performed physical exercise is indicated by statistically processing registered sensations. The invention also relates to a recovery measuring device to be utilised in the method and a computer program to be used in the measuring device.

BACKGROUND

During physical exercise the stress level a person's nervous muscular system experiences varies. In order for the exercise to be effective, it is good to know what kind of physical stress a person's nervous muscular system or some part of it has undergone during the exercise. In addition to the stress level, it is good to know the person's recovery from the performed exercise, whether it is a question of a top athlete or a person keeping fit. If the person does not recover from the performed exercise, he may due to excessive exercise end up in a state of overtraining. This may lead to mandatory resting, which may last from weeks up to months. Especially for top athletes a state of overtraining due to exercise is a very undesired phenomenon.

A person's own subjective sensation of stress and recovery therefrom has been found to be insufficient.

There are various measuring arrangements for measuring the fitness state of an exercising person. The aerobic fitness, i.e. the fitness associated with the heart, lungs and circulation, describes the amount of oxygen pumped by the heart and transported to the muscles and the ability of the muscles to utilise the oxygen they receive. The aerobic fitness is especially associated with endurance sports.

A heart rate monitor with its heart rate analysis can for example be used for measuring aerobic fitness. Heart rate analysis is used to measure the effect of many bodily occurrences on the heart rate, which is regulated by the autonomic nervous system. The regulation of the autonomic nervous system can be disturbed due to hard exercise or psychological stress. A serious state of overstrain caused by exercise can be seen in the autonomic nervous system also during rest.

In the autonomic nervous system the stress and overtraining are often only seen with a delay, wherefore the strain of the exercise may have been too straining for a long time, before the situation is observed. Thus correcting procedures may take time.

One way to measure a person's fitness and recovery is to sufficiently often do blood tests in connection with exercises or after them. Such a measuring method is however difficult to utilise. Additionally measurements performed from blood are complex and expensive to perform for a common person keeping fit.

Recovery can be measured with extensive blood tests, which measure for example lactate and creatine kinase. Lactate is a product of glucose metabolism, which is produced in the muscles especially as a result of anaerobic muscle work. Creatine kinase is a common enzyme in muscle cells.

When a muscle is damaged due to exercise or some other reason, creatine kinase is released from the muscle cells into the blood. The larger the damage, the more the measuring value of the creatine kinase measured with a blood test rises. Similarly, if an untrained person suddenly uses his muscles vigorously, the associated muscle pain and mild muscle damage increases the measuring value of the creatine kinase.

In order to optimise the end result of the exercise, the person performing the exercise must find the right ratio between exercise and recovery. Thus tiredness and tissue damage caused by hard exercise is prevented. Depending on the degree of difficulty of the exercise, the person performing the exercise on average needs a time period of two days to two weeks to recover from a straining exercise.

Supercompensation is a change generated by training and recovery therefrom in the performance of an athlete, as a result of which the performance is momentarily above the normal level. A well-timed new exercise thus provides a rising development in the performance of the person performing the exercise.

Both the performed exercise and the recovery from the exercise, in practice the rest, have an important part in the phenomenon of supercompensation. An exercise taking place too early or being too hard before the recovery from the last exercise leads to a state of overtraining. In order to achieve the state of supercompensation the person performing the exercise must optimise his exercise so that the recovery time from the last exercise is not too long or too short.

Various treatment devices based on electrical stimulation are used for treating a damage or imbalance in the nervous muscular system arisen as a result of illness, injury or over exercise. The treatment device is used to lead electric current into the part of the nervous muscular system to be treated.

For example Finnish patent FI 120575 describes an electric treatment device and treatment arrangement, by using which the electricity treatment given to a patient can be made more effective. In the method described in patent FI 120575, the most suitable frequency of the treatment current and the most suitable strength of the treatment current for the patient are first determined. When these variables are determined, these variables are used to treat the patient's muscle damage. The aim of the treatment is to with the aid of electricity treatment return the metabolism of the object being treated, for example a certain muscle, to a level, which corresponds to the metabolism of a healthy muscle. The success of the treatment is indicated by the fact that a treatment current of a certain frequency reaches some predetermined threshold value. The method can thus speed up the improvement of the nervous muscular system being treated.

Other various devices and methods suited for treatment of the function of either nerves or muscles are presented in the following publications: CN 1029505, CN 101612450 and U.S. Pat. No. 7,254,444. The references describe methods and devices, which can be used to treat either damaged or overstressed tissues in the body.

Recovery is a result of partly nervous and partly metabolic factors. There has so far not been a reliable method of measuring anaerobic recovery or state of acute recovery of nerves and muscles without extensive blood tests.

SUMMARY

It is an object of the invention to present a new method and device arrangement, by using which the stress level of physical exercise and the level of recovery from the exercise can be determined with an electric recovery measuring device as reliably as with blood tests.

The objects of the invention are attained with a measuring method and device, where changes caused by physical stress in the nervous muscular system are indicated and repeatedly analysed. The analysis utilises sensations caused by interference currents of different frequencies and with varying current strengths in a certain part of the nervous muscular system of the performer of the exercise. The strain caused by the exercise affects how strong an interference current needs to be fed into the examined part of the nervous muscular system in order to achieve a certain predetermined physical sensation.

It is an advantage of the invention that the stress level caused by the exercise and the recovery level can be indicated with a non-invasive measuring device.

It is further an advantage of the invention that the measuring of the stress level and recovery level can be performed at other times than during the performance.

It is further an advantage of the invention that the measuring of the stress level and/or the recovery level can be done at any time or place.

It is further an advantage of the invention that the measuring information of the stress level and recovery level are discovered more quickly than with blood analyses.

It is further an advantage of the invention that the measuring of the stress level and recovery level can be performed independently by each exercising individual without the presence of medical personnel.

The method according to the invention for indicating a state of overstress in a nervous muscular system, in which method an interference current, the frequency and current strength of which can be adjusted, is fed into a part of the nervous muscular system, is characterised in that the method comprises calculating a measurement-specific average strength of the interference current for each predetermined physical response in the examined part of the examined nervous muscular system normalising the measurement-specific average interference current for each physical response or response group and indicating a state of overstress in the nervous muscular system, if some measurement-specific normalised average of the interference current does not fulfil a set statistical criteria.

The recovery measuring device according to the invention, which indicates a state of overstress in the nervous muscular system, which device comprises means for feeding an interference current, the frequency and current strength of which can be determined, to the nervous muscular system and which has means for storing those frequencies and current values of the interference current, which cause one of a set of predetermined physical responses in the nervous muscular system, is characterised in that the recovery measuring device comprises means for calculating a measurement-specific average of the strength of the interference current for each predetermined physical response in the nervous muscular system means for normalising the measurement-specific calculated average interference current for each physical response, and means for indicating a state of overstress in the nervous muscular system, if some measurement-specific normalised average of the interference current for the physical response does not fulfil a preset statistical criteria.

Some advantageous embodiments of the invention are presented in the dependent claims.

The basic idea of the invention is the following: The nervous muscular system or a part of it which has been the object of physical exercise or stress, is irritated with an interference current. Several frequencies and current strengths of the interference current are advantageously used in the irritation. The measuring object can advantageously be the tissues of the extremities or the back. Measuring information can thus always be obtained from two functionally similar parts of the nervous muscular system and from the responses given by them for the measuring. This is advantageous because a possibly one-sidedly stressed body part does not distort the results or a body part, which is incorrectly strained during exercise, is discovered.

In the method according to the invention the recovery level measurings are advantageously done with at least one interference current frequency. With each interference current frequency three different responses or response groups caused by the interference current are searched for in the examined part of the nervous muscular system by gradually increasing the interference current.

The first sensation caused by the interference current is called a sensory response. In the sensory response the effect caused by the used interference current in the nervous muscular system is such that the examined person perceives a tingling caused by the interference current. In the sensory response, three different sensory responses or sensations, i.e. first tingling, clear tingling and strong tingling, are advantageously achieved by increasing the interference current.

The second sensation caused by the interference current is called a motoric response. The interference current used in the motoric response causes a discernible muscle contraction in the examined nervous muscular system. In the motoric response, three different motoric responses, i.e. weak muscle contraction, clear muscle contraction and strong muscle contraction, are advantageously achieved by increasing the interference current.

The third sensation caused by the interference current is a pain response. The interference current used in the pain response causes the examined person to experience an unpleasant feeling in the examined part of the nervous muscular system.

In the first step a measurement-specific average is calculated for each of the three sensations/responses (sensory, motoric, pain) of the part of the nervous muscular system. The average includes measuring values obtained at all the used measuring frequencies of the interference current. Additionally a measurement-specific average of all the measurings is advantageously calculated.

In the second step the sensation-specific average of a single measurement is normalised by dividing it with a sensation-specific long-term average.

Based on the central limit theorem the distribution of averages of the measuring results of the measuring arrangement according to the invention complies with the normal distribution to a sufficient degree. Physical stress and poor recovery therefrom cause a deviation in the measurement-specific normalised average, which deviation is outside the 1σ variation range of the normal distribution. Such a measuring result shows that the nervous muscular system or part thereof has experienced a stress, from which it has not yet recovered. By doing measurements for example on subsequent days, it can with the aid of the recovery measuring device and recovery monitoring method according to the invention be indicated how quickly the nervous muscular system recovers from the caused stress state.

BRIEF DESCRIPTION OF THE DRAWINGS

In the following, the invention will be described in detail. In the description, reference is made to the appended drawings, in which

FIG. 3a shows an example of sensation-specific individual measuring values of interference currents obtained with a recovery measuring device according to the invention, measured during a month.

DETAILED DESCRIPTION OF THE DRAWINGS

The embodiments in the following description are given as examples only and someone skilled in the art can carry out the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

Figure 1:
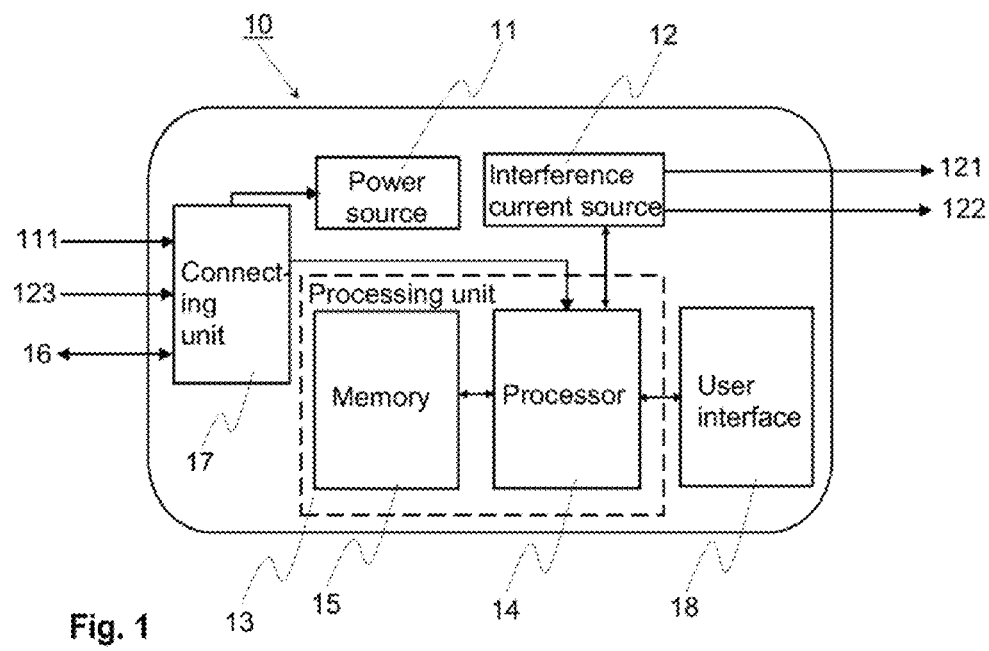
FIG. 1 shows as an example a flowchart of a recovery test device according to the invention.

FIG. 1 shows as an example a recovery measuring device 10 according to the invention. The recovery measuring device 10 comprises a power source 11 for satisfying the electric power required by a processing unit 13, a user interface 18 and an interference current source 12. The power source 11 may advantageously be an accumulator or a battery.

The recovery measuring device 10 advantageously also comprises a connecting unit 17. The connecting unit 17 comprises means, through which the accumulator of the power source 11 of the recovery measuring device 10 can be charged from some external power source 111. The connecting unit 17 also comprises means with the aid of which the recovery measuring device 10 according to the invention can be connected to some external data processing device 16. Data transfer to the external data processing device 16 can be handled either via a cable or with a wireless data transfer connection. The wireless data transfer connection can be implemented for example with an infrared, a Bluetooth or a ZigBee connection. The connecting unit 17 also comprises means, through which the recovery measuring device 10 according to the invention is connected to a feedback means 123 on the examined person.

The recovery measuring device 10 advantageously also comprises a user interface 18. The user interface 18 advantageously comprises adjustment/control means (FIG. 2 references 152 and 153), which can be used to determine the strength and frequency of the interference current to be used in the measurings. These adjustment means may for example be adjustment knobs, sliding switches or action buttons on a touch screen. The user interface 18 advantageously also comprises display means (FIG. 2 reference 151), by means of which the measuring results can be shown during or after the measuring event.

The processing unit 13 of the recovery measuring device 10 advantageously comprises a suitable processor 14 or a programmable logic and a thereto connected memory 15. The memory 15 can utilise either non-volatile and/or volatile memory technology. The computer program to be utilised in the recovery indication arrangement according to the invention is advantageously stored in the memory 15. The processor 14, the memory 15 and the computer program stored in the memory 15 are arranged to determine and indicate the current state of the nervous muscular system based on the performed nervous muscular system measurings. Measuring results describing the stress state and/or recovery of the nervous muscular system can also at least temporarily be stored in the memory 15.

The processing unit 13 receives control commands from the user interface 18. The activity of the interference current source 12 is advantageously controlled with these control commands. The given control commands can be used to set the interference current frequency, the interference current strength to be used at any time and to start and stop the measuring event. The processing unit 13 can also receive control commends sent from some external data processing device, which commands are received through the connecting unit 17. The processing unit 13 can through the connecting unit 17 also send information to some external data processing device 16 regarding when the measuring was performed and what the measuring results were.

The interference current source 12 is able to form an interference current in accordance with the control command received from the processing unit 13. The interference current source 12 edits the frequency and current strength of the interference current in accordance with the received control command. When it has received the measuring command given with the aid of the user interface 18, the interference current source 12 steers the interference current via the connections 121 and 122 to the part of the nervous muscular system, which is the object of the measuring.

In one advantageous embodiment of the invention the interference current source 12 is a separate device with its own power source. In this embodiment the interference current source 12 is connected for example to a PC, which controls the activity of the interference current source.

In one advantageous embodiment of the invention the person being examined can advantageously enter information with the feedback device 123 regarding when a certain sensation can be perceived in the examined part of the nervous muscular system. The information about the experienced sensation is conveyed to the recovery measuring device 10 via a data transfer connection 123a, which is connected to the connecting unit 17. The data transfer connection 123a can be implemented either via a cable or with a wireless data transfer connection. The wireless data transfer connection can be implemented for example with infrared, Bluetooth or ZigBee technology.

In another advantageous embodiment of the invention the person being examined enters feedback information regarding the sensation by using the user interface 18 in the recovery measuring device.

Figure 2:
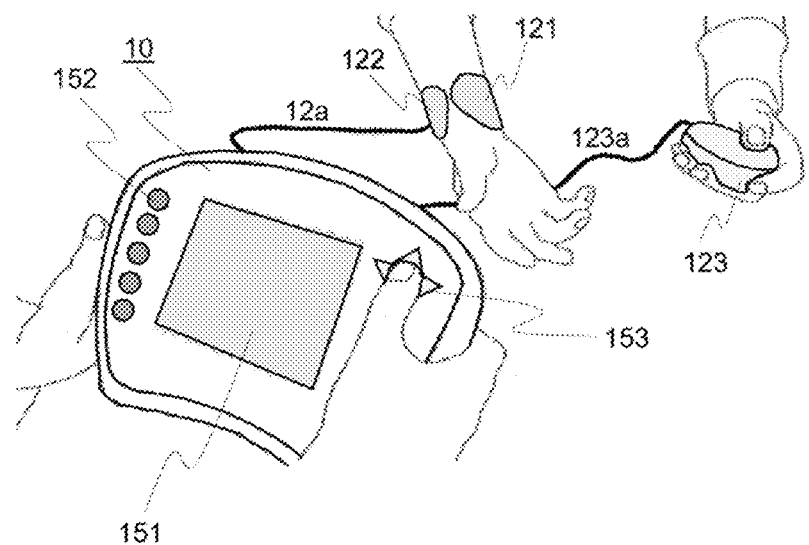
FIG. 2 shows as an example a recovery measuring arrangement according to the invention.

FIG. 2 shows an exemplary measuring situation of the nervous muscular system. In FIG. 2 the recovery measuring device 10 is used to perform measurings of the nervous muscular system in the right arm of the test person. Measuring electrodes 121 and 122 of the recovery measuring device 10 have using a cable 12a been connected to the person's right arm. The person controlling the measuring sets at all times the frequency and current strength of the interference current to be used with control means 152 and 153 belonging to the user interface 18 of the recovery measuring device 10.

In one measuring event of the nervous muscular system according to the invention three different measuring frequencies are used, which are advantageously 10 Hz, 50 Hz and 100 Hz. Several separate measurings are advantageously done at each said measuring frequency, the results of which are stored in the memory 15 of the recovery measuring device 10. In each measuring the value and used frequency of the interference current is stored, with which a certain response or sensation was obtained. Three different responses or response groups are advantageously utilised as sensations obtainable from the nervous muscular system, and they are sensory response (S), motoric response (M) and pain response (P).

The first sensation caused by the interference current is called a sensory sensation (S). In the sensory response, three different sensory responses or sensations, i.e. first tingling (1S), clear tingling (2S) and strong tingling (3S), are advantageously achieved by increasing the interference current. In the sensory sensation the effect caused by the used interference current in the nervous muscular system is such that the examined person in the example in FIG. 2 perceives in his right arm a tingling of a varying degree caused by the interference current.

The second sensation, a sensation achieved with a higher interference current, is called a motoric sensation (M). In the motoric response, three different motoric responses, i.e. weak muscle contraction (4M), clear muscle contraction (5M) and strong muscle contraction (6M), are advantageously achieved by increasing the interference current. The interference current used in the motoric sensation causes a discernible involuntary muscle contraction in the examined nervous muscular system. Such a motoric sensation may for example be the involuntary bending of a finger in the right hand shown in FIG. 2.

The third sensation, a sensation achieved with the highest interference current, is pain (7P). The interference current used in the pain sensation causes the examined person to experience an unpleasant feeling in the examined part of the nervous muscular system, such as in the right arm in the example of FIG. 2.

In the exemplary embodiment shown in FIG. 2 three different sensations are with three different frequencies indicated from the right arm. The sensory and motoric sensation are advantageously caused several times, for example three times, so that different degrees of responses can be indicated within the sensation. The third sensation, pain, is advantageously indicated only once, When all the measurings of the right arm shown in FIG. 2 have been performed, the same measurings are done also on the left arm of the test person.

In the example of FIG. 2 when the responses in the nervous muscular system to the given interference currents have been measured from both arms, then the recovery measuring device 10 calculates a sensation-specific average advantageously of all values of the interference current, which have been measured from the right and left arm. Additionally a common average of all three different sensations measured from both arms can advantageously be calculated. In the next step the calculated averages are normalised. If the average of a single sensation or all sensations obtained in a single measurement is not within the 1σ variation range of the normal distribution formed by the normalised averages, then the nervous muscular system has not recovered from the performed physical exercise.

In the example in FIG. 2 the state of the nervous muscular system is indicated from certain tissues in the arms. In a second advantageous embodiment of the invention the state of the nervous muscular system is measured from certain tissues in the legs. In a third advantageous embodiment of the invention the state of the nervous muscular system is measured from tissues on both sides of the spine. In a fourth advantageous embodiment of the invention the state of the nervous muscular system is measured only from a right- or left-side extremity.

Figure 3A:
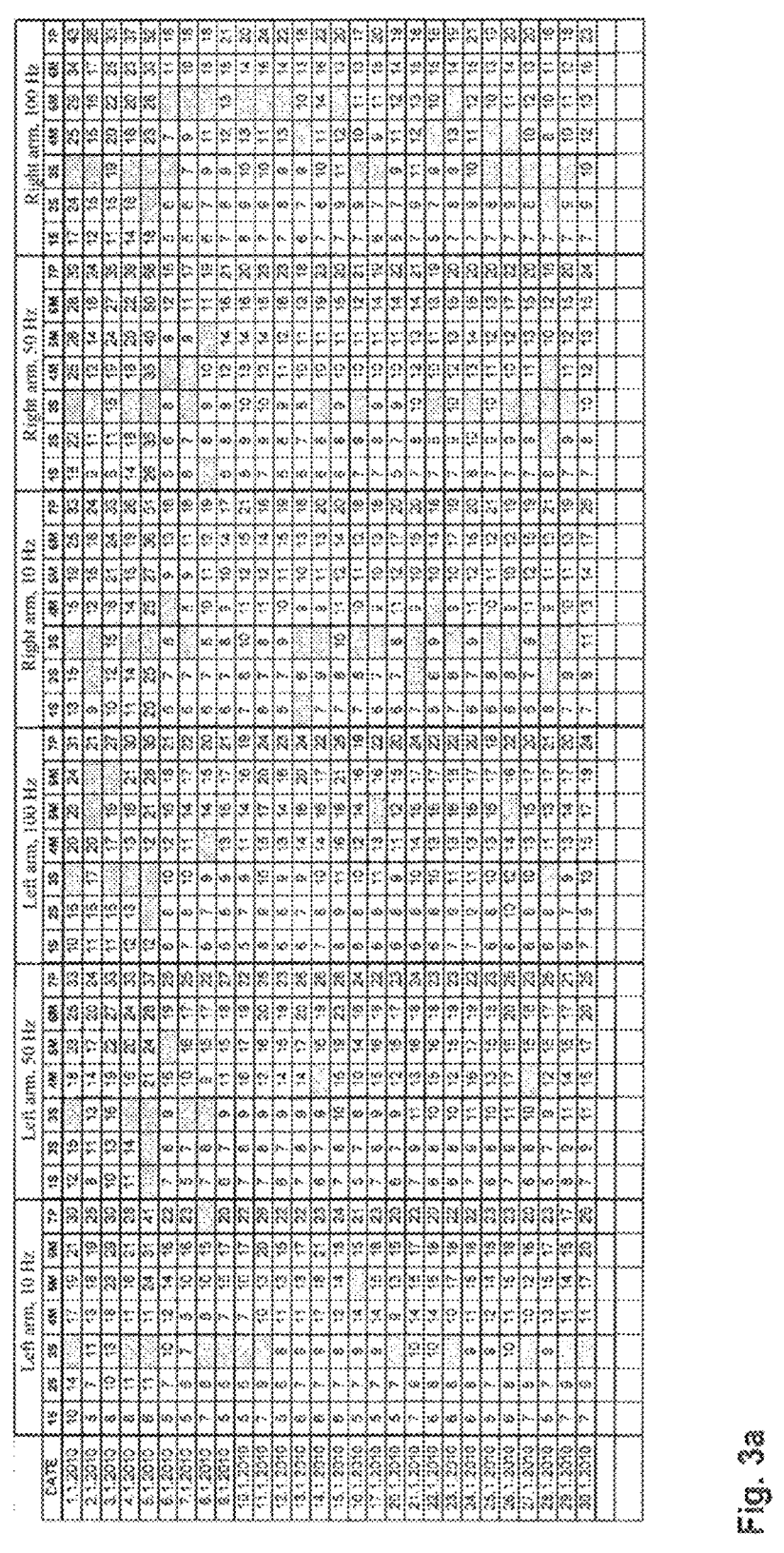
Figures 3B, 3C, 4A, 4B:
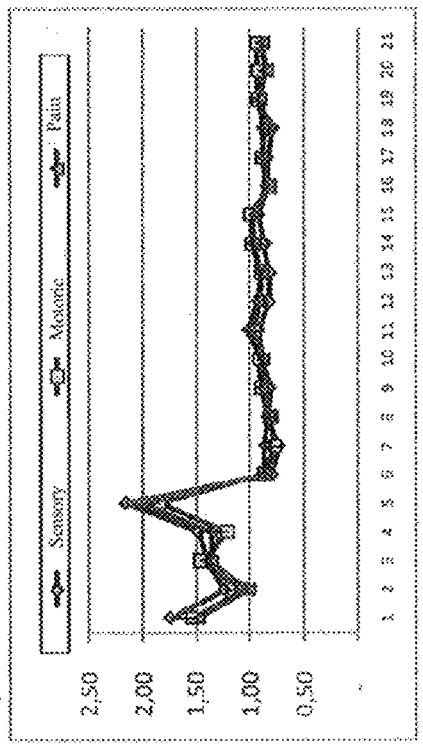
FIG. 3b shows sensation-specific averages of the interference current calculated from the individual interference current values of the table in FIG. 3a and the averages of all the sensation-specific interference currents per measurement.
FIG. 3c shows normalised averages of the sensation-specific interference current averages of FIG. 3b and a normalised average of all the sensation-specific averages per measurement.
FIG. 4a shows normalised graphs of the averages of the sensation-specific interference currents included in FIG. 3c as a function of the measurements.
FIG. 4b shows a normalised graph of the average of the sensation-specific averages included in FIG. 3c as a function of the measurements.

FIGS. 3a, 3b and 3c show as exemplary tables the results of measurings done with the recovery measuring device 10 according to the invention and averages and normalised averages calculated from them.

FIG. 3a shows individual results of the performed measurings. Column "DATE" shows the day each measuring was done. One row in the table represents the measurings done during one measurement. In the example in FIG. 3a the measurings are done during the time between 1 Jan. 2010 and 30 Jan. 2010. There have all together been 28 measurements. The first, third and fifth measurement are measurings done after exercise.

The table in FIG. 3a has six main columns, three of which concern the measurings of the left arm and the remaining three of which concern the measurings of the right arm. The table shows that both arms have undergone measurings at frequencies of 10 Hz, 50 Hz and 100 Hz. At all three frequencies, three measurings achieving three different sensory responses have been made (1S, 2S and 3S). In the same way, at all three frequencies, three measurings achieving three different motoric responses have been made (4M, 5M and 6M). Only one measuring of the pain response has been done at each of the three frequencies (7P). The empty cells in the table of FIG. 3a shows that either a measuring result has not been obtained or the measuring result has not been stored in the memory 15 of the recovery measuring device 10.

The table shown in FIG. 3b shows measurement-specific averages calculated from the averages in table 3a in columns $S_{aver}$, $M_{aver}$, and $P_{aver}$ for all sensations S, M and P. Additionally it shows a common average of the averages $S_{aver}$, $M_{aver}$ and $P_{aver}$ of measurement-specific sensations in column "All". Additionally averages $S_{ka}$, $M_{ka}$, $P_{ka}$ of all sensation-specific averages $S_{aver}$, $M_{aver}$, $P_{aver}$ and an average $R_{ka}$ of their common average "All" are shown in the bottom edge of the table 3b.

The table in FIG. 3c shows normalised averages $S_{pi}$, $M_{pi}$, $P_{pi}$ and $R_{pi}$ of the averages $S_{aver}$, $M_{aver}$, $P_{aver}$ and "All" shown in the table in FIG. 3b. The normalised averages shown in the table in FIG. 3c are obtained by dividing the sensation-specific average $S_{aver}$, $M_{aver}$, $P_{aver}$ and "AU" of a single measurement with the corresponding average $S_{ka}$, $M_{ka}$, $P_{ka}$ or $R_{ka}$ of all the measurements.

FIG. 4a shows the normalised averages $S_{pi}$, $M_{pi}$ and $P_{pi}$ of the table in FIG. 3c as a function of the measurements. All the graphs of the normalised averages have a corresponding shape. The first five points represent a situation right after exercise, when the nervous muscular system has not yet returned to its normal state. The rest of the measurements 6-21 represent a situation, when the nervous muscular system has completely recovered. Only in the recovered state the mean deviation σ of the average $S_{pi}$ is 0.062023, the mean deviation σ of the average $M_{pi}$ is 0.061144, the mean deviation σ of the average $P_{pi}$ is 0.055314.

FIG. 4b shows the normalised average "All" of the table in FIG. 3c as a function of the measurements. When the nervous muscular system is in a recovered state, the mean deviation σ of the average "All" is 0.05099.

The graphs in FIGS. 4a and 4b make it clear that the measuring results, which have been obtained either directly after exercise or before the nervous muscular system has recovered, measurements 1-5, are all outside the 1σ variation range calculated from the normalised averages in every graph shown in FIGS. 4a and 4b. The recovery measuring device 10 according to the invention indicates such measuring results expressing a lack of recovery.

Figure 5:
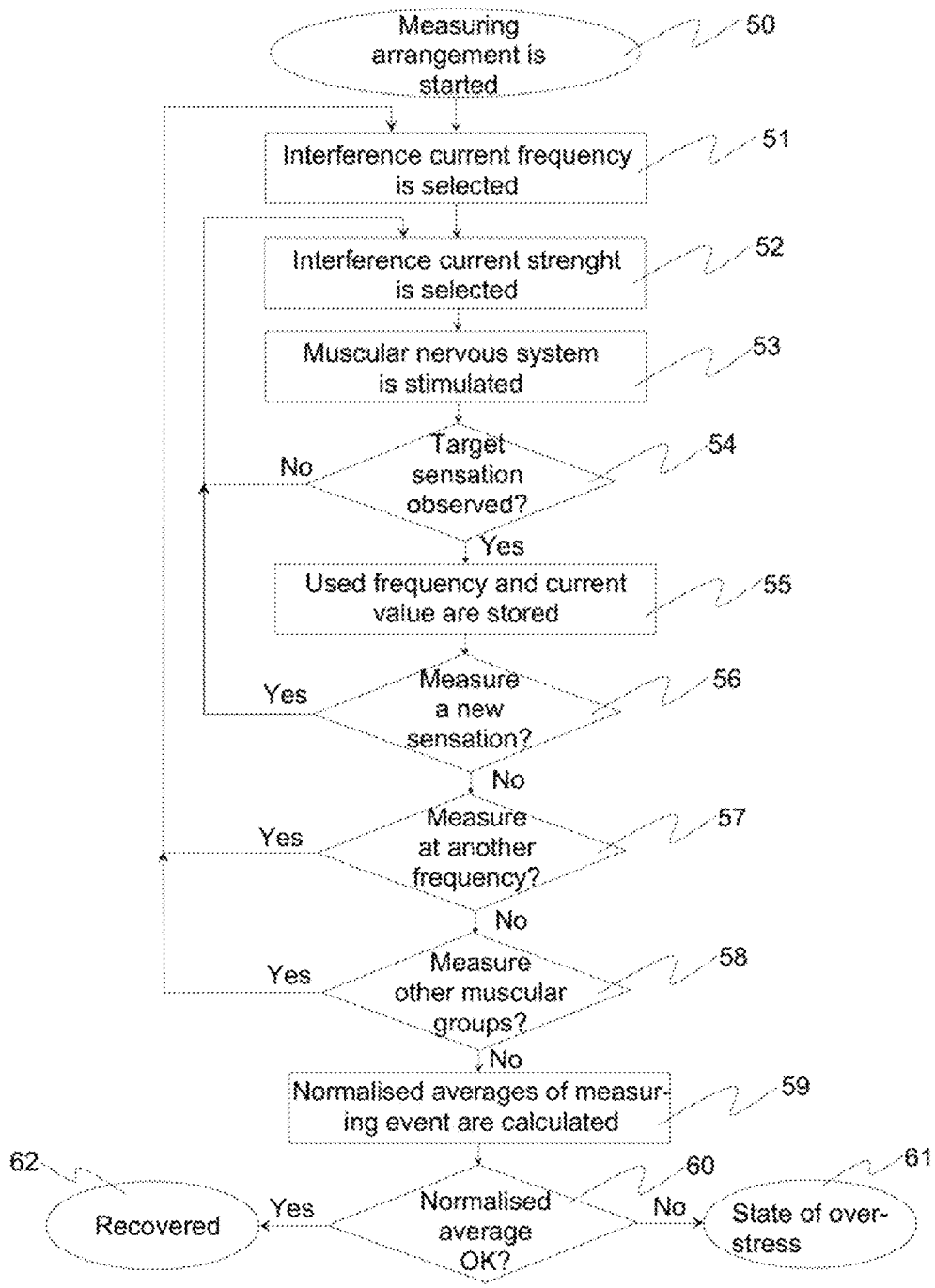
FIG. 5 shows as an exemplary flowchart some main steps of the measuring method according to the invention, which indicates recovery.

FIG. 5 shows as an exemplary flowchart the main steps used for determining and indicating the state of the nervous muscular system according to the invention.

The measuring of the nervous muscular system is started in step 50. The measuring sensors of the recovery measuring device 10 are connected to the part of the nervous muscular system to be examined and the recovery measuring device is started.

In step 51 the interference current frequency to be used in the next measuring is selected. In one advantageous embodiment of the invention 10 Hz, 50 Hz and 100 Hz are used as the measuring frequencies of the interference current. One measuring uses only one of the above-mentioned frequencies at a time.

Next in step 52 the strength of the interference current to be fed into the nervous muscular system is set. At each frequency the measuring of the target response or sensation is advantageously begun at a low current value, which is advantageously less than 10 mA. By using a small current value it is attempted to advantageously first achieve a first-degree sensory sensation 1S in the nervous muscular system.

In step 53 the nervous muscular system is irritated with the interference current defined in steps 51 and 52.

In step 54 the person, who is the object of the measuring, gives feedback regarding his sensation. If the intended response or sensation, alternatively 1S, 2S, 3S, 4M, 5M, 6M or 7P has not been achieved, the measuring process returns to step 52, where a new higher value for the strength of the interference current is set. Thereafter in the step 53 the nervous muscular system is irritated with the stronger interference current. If in step 54 the target sensation is still not observed, the process again returns to step 52. The loop 52-54 is repeated so many times, that the target response or sensation, either 1S, 2S, 3S, 4M, 5M, 6M or 7P, is observed in the examined nervous muscular system.

When the target sensation, either 1S, 2S, 3S, 4M, 5M, 6M or 7P, is finally observed in step 54, then in step 55 the used frequency and current value of the interference current are stored in the memory 15 of the recovery measuring device 10. The storing is advantageously either performed by the user/test person of the recovery measuring device 10 by using the user interface of the recovery measuring device or alternatively the signal the test person gives with the feedback device 123 causes the storing.

In one advantageous embodiment of the invention the motoric response of the test person is indicated from the test person with motion sensors and the indicated motoric response is automatically stored in the memory 15 of the recovery measuring device 10.

In step 56 a decision is made regarding a new measuring of the sensation. The loop 52-56 is advantageously repeated so many times, that all the sensory, motoric and pain responses, for example the responses 1S, 2S, 3S, 4M 5M, 6M or 7P, have been measured. The three different responses with their subclasses mentioned in the description above are only examples, and the invention is not limited to the mentioned amounts. Thus the measuring of each response can for example comprise only one measurement or more measurements than the above-mentioned three measurements.

After measuring and indicating the pain sensation P, the process moves from step 56 to step 57, because all three sensations S, M and P with their subclasses have been measured and indicated at one frequency of the interference current. In step 57 a decision is made regarding whether interference current measurings have been done on all measuring frequencies or not.

If it is in step 57 found that any of the exemplary frequencies 10 Hz, 50 Hz or 100 Hz of the interference current is not yet measured, the measuring process advantageously returns to step 51. Thereafter the loops 52-54 and 52-56 are repeated, so many times that all three sensations the sensory sensation S, the motoric sensation M and the pain sensation P are measured also at this frequency.

When the measurings of the nervous muscular system are done at all selected frequencies of the interference current regarding all sensations S, M and P with their subclasses, then the process moves from step 57 to step 58. In step 58 a decision is made regarding whether measurings are to be made also from another part of the body. A measuring from the other hand, other foot or the back can for example come into question.

If a decision is made in step 58 to measure some other body part, the measuring process returns to step 51. From step 51 the measuring process advances in the above-described way, until it finally again arrives at step 58.

If it is in step 58 decided that no other body parts are to be measured, the measuring process continues to step 59. In step 59 the measurement-specific averages $S_{aver}$, $M_{aver}$, $P_{aver}$ for each target sensation and the common average "All" of the sensations are first calculated. Thereafter the measurement-specific averages $S_{aver}$, $M_{aver}$, $P_{aver}$ and the common average of the sensations are normalised by dividing them with the corresponding average $S_{ka}$, $M_{ka}$, $P_{ka}$ or $R_{ka}$ of all the measurements. The calculated normalised averages $S_{pi}$, $M_{pi}$, $P_{pi}$ and $R_{pi}$ are stored in the memory 15 of the recovery measuring device 10.

Thereafter in step 60 the normalised average is compared to the person's long-term distribution of averages of the normalised measuring values. If the normalised average of the measurement (either the average of a single sensation or the common average of all sensations) is outside said 1σ variation range of the normalised average distribution, then the nervous muscular system has not recovered from the performed exercise, step 61. If the normalised average is within the 1σ variation range of the normalised average distribution, then the nervous muscular system has recovered from the performed exercise, step 62. The recovery measuring device 10 according to the invention indicates both alternative results to the user of the recovery device 10.

It is clear to someone skilled in the art that the steps shown in the flowchart of FIG. 5 can also be realised in some other order than what is described above. For example whether some sensation is first measured several times before the frequency of the interference current is altered, can also be realised so that a certain sensation is first measured at all frequencies of the interference current. Thereafter one returns to the original utilised frequency of the interference current and repeats the same sensation measuring at all the frequencies of the interference current. When this loop has been carried out enough times, the same number of measuring results have been obtained as what is shown in connection with the description of flowchart 5.

It is further clear to someone skilled in the art that there can be one, two or more measuring frequencies than the three exemplary frequencies 10 Hz, 50 Hz and 100 Hz mentioned above.

All the above-described steps of the measuring and indication process can also be realised with computer program commands, which are executed in a suitable general or special-purpose processor. The computer program commands can be stored in a computer-readable media, such as a data disk or a memory, from where the processor can retrieve said computer program commands and execute them. The references to computer-readable media can for example also contain special components, such as programmable USB Flash memories, logic arrays (FPLA), application-specific integrated circuits (ASIC) and signal processors (OSP).

Some advantageous embodiments of the method and device according to the invention have been described above. The invention is however not limited to the embodiments described above, but the inventive idea can be applied in numerous ways within the scope of the claims.

The invention claimed is:

1. A method for indicating a state of overstress in a nervous muscular system, the method comprising:
   steering an interference current into a part of the nervous muscular system, a frequency and a current strength of the interference current being adjustable;
   receiving feedback identifying at least one target response from a plurality of predetermined physical responses in an examined part of the nervous muscular system;
   storing a frequency value and a current strength value of the interference current which caused the at least one target response;
   calculating a measurement-specific average strength of the interference current for each identified target response from the plurality of predetermined physical responses in the examined part of the nervous muscular system,
   normalising the measurement-specific average strength of the interference current for each identified target response, and
   indicating a state of overstress in the nervous muscular system, if a measurement-specific normalised average strength of the interference current does not fulfil a set statistical criteria.

2. The method according to claim 1, wherein the predetermined physical responses comprise at least one of a sensory response, a motoric response and pain.

3. The method according to claim 2, wherein the physical responses indicating the nervous muscular system comprise a response group, which comprises several physical responses of varying degrees.

4. The method according to claim 3, further comprising identifying each of the predetermined physical responses of sensory response, motoric response and pain at least at one frequency value of the interference current.

5. The method according to claim 4, further comprising indicating the sensory response and the motoric response at least once at each frequency value of the interference current.

6. The method according to claim 5, further comprising calculating measurement-specific averages for each of the predetermined physical responses and a common average of the indicated physical responses, which are normalised by dividing each of the measurement specific averages separately with a corresponding average of all the measurements, whereby normalised measurement-specific averages of each of the predetermined physical responses are obtained.

7. The method according to claim 6, further comprising indicating that the examined part of the nervous muscular system is recovered from the exercise, if the normalised measurement-specific averages of each of the physical responses are within a 1σ-variation range of the normal distributions of corresponding averages of all the measurements.

8. A recovery measuring device, which comprises means for steering an interference current into a nervous muscular system, the frequency and current strength of the interference current being adjustable, wherein the measuring device further comprises:
   a feedback device for giving information regarding when a certain target response for a plurality of predetermined physical responses in the nervous muscular system has been observed;
   means for storing at least one frequency value and at least one current value of the interference current, causes the observed certain target response;
   means for calculating a measurement-specific average of the stored current value of the interference current for each of the predetermined physical responses of the plurality;
   means for normalising the calculated measurement-specific average of the interference current for each of the predetermined physical responses, and
   means for indicating a state of overstress in the nervous muscular system, if some measurement-specific normalised average of the interference current for at least one of the predetermined physical responses does not fulfil a preset statistical criteria.

9. The recovery measuring device according to claim 8, wherein the means for indicating a state of overstress in the nervous muscular system comprises a processor, a memory and a computer program stored in the memory, which are arranged to determine and indicate the current state of the nervous muscular system based on the normalised averages of the interference currents.

10. The recovery measuring device according to claim 9, wherein the means for indicating a state of overstress in the nervous muscular system are arranged to indicate that the nervous muscular system is recovered from an exercise, if the normalised measurement-specific averages of the physical responses are within a 1σ variation range of the normal distributions of corresponding averages of the interference current for all measurements.

11. A computer software product, comprising computer program code means stored on a computer-readable storage means, which code means are arranged to steer an interference current into a part of the nervous muscular system, the frequency and current strength of the interference current being adjustable, receive feedback identifying a target response from a plurality of predetermined physical responses in an examined part of the nervous muscular system, store a frequency value and a current strength value of the interference current which caused the at least one target response in the examined part of the nervous muscular system, calculate a measurement-specific average strength of the interference current for each identified target response from the plurality of predetermined physical responses in the examined part of the nervous muscular system, normalize the measurement-specific average strength of the interference current for each identified target response, and indicate a state of overstress in the nervous muscular system, if a measurement-specific normalised average of the interference current does not fulfil a set statistical criteria when said program is run on a computer.

* * * * *